US011559790B2

(12) United States Patent
Luo et al.

(10) Patent No.: US 11,559,790 B2
(45) Date of Patent: Jan. 24, 2023

(54) RECONSTITUTED DEHYDROGENATION CATALYST SHOWING SLOWED ACTIVITY LOSS WHEN COMPARED WITH FRESH CATALYST

(71) Applicant: Dow Global Technologies LLC, Midland, MI (US)

(72) Inventors: Lin Luo, Sugar Land, TX (US); Devon C. Rosenfeld, Houston, TX (US); Andrzej M. Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 8 days.

(21) Appl. No.: 17/137,978

(22) Filed: Dec. 30, 2020

(65) Prior Publication Data

US 2021/0129117 A1    May 6, 2021

Related U.S. Application Data

(62) Division of application No. 14/366,611, filed as application No. PCT/US2013/024831 on Feb. 6, 2013.

(60) Provisional application No. 61/600,764, filed on Feb. 20, 2012.

(51) Int. Cl.
| | |
|---|---|
| *B01J 23/62* | (2006.01) |
| *B01J 38/48* | (2006.01) |
| *B01J 23/96* | (2006.01) |
| *C07C 5/333* | (2006.01) |
| *C07C 5/32* | (2006.01) |

(52) U.S. Cl.
CPC ............. *B01J 23/62* (2013.01); *B01J 23/96* (2013.01); *B01J 38/485* (2013.01); *C07C 5/322* (2013.01); *C07C 5/3337* (2013.01); *C07C 2521/12* (2013.01); *C07C 2523/04* (2013.01); *C07C 2523/08* (2013.01); *C07C 2523/42* (2013.01); *C07C 2523/62* (2013.01); *C07C 2527/224* (2013.01); *Y02P 20/52* (2015.11); *Y02P 20/584* (2015.11)

(58) Field of Classification Search
CPC .......... B01J 38/12; B01J 38/485; B01J 23/62
USPC ..................... 502/22, 56, 334, 339
See application file for complete search history.

(56) References Cited

U.S. PATENT DOCUMENTS

| | | | |
|---|---|---|---|
| 2,479,109 A | 8/1949 | Haensel | |
| 2,862,890 A | 12/1958 | Daugherty et al. | |
| 3,060,133 A * | 10/1962 | Meier ................. | C01B 21/1418 423/22 |
| 3,140,263 A | 7/1964 | Payne | |
| 3,140,264 A | 7/1964 | Oleck et al. | |
| 3,259,588 A | 7/1966 | Harvey et al. | |
| 3,882,159 A | 5/1975 | Callahan et al. | |
| 4,118,339 A * | 10/1978 | Latos ................. | B01J 21/20 502/25 |
| 4,147,660 A | 4/1979 | Yamauchi et al. | |
| 4,409,122 A | 10/1983 | Kleuskens et al. | |
| 4,422,954 A | 12/1983 | Van Peppen | |
| 6,777,451 B2 | 8/2004 | Koveal et al. | |
| 6,800,579 B2 | 10/2004 | Daage et al. | |
| 7,235,706 B2 | 6/2007 | Iezzi et al. | |
| 7,473,668 B2 * | 1/2009 | Bartolini ................. | B01J 23/96 502/355 |
| 2003/0191351 A1 | 10/2003 | Voskoboynikov et al. | |
| 2004/0242945 A1 * | 12/2004 | Pelati ................. | B01J 37/0205 585/444 |
| 2005/0177016 A1 | 8/2005 | Sanfilippo et al. | |
| 2008/0194891 A1 | 8/2008 | Pretz et al. | |
| 2009/0258779 A1 | 10/2009 | McCarthy et al. | |
| 2009/0261019 A1 | 10/2009 | McCarthy et al. | |
| 2010/0236985 A1 | 9/2010 | Luo et al. | |
| 2012/0123177 A1 | 5/2012 | Pretz et al. | |

FOREIGN PATENT DOCUMENTS

| | | | | |
|---|---|---|---|---|
| CA | 1292248 C | * | 11/1991 | ............. B01J 23/58 |
| CN | 1141218 A | | 1/1997 | |
| GB | 1185246 A | | 3/1970 | |
| GB | 1499297 A | * | 1/1978 | ............. B01J 23/62 |
| KR | 2012 0077688 | * | 7/2012 | ............ B01J 27/125 |
| WO | 2005077867 A2 | | 8/2005 | |
| WO | WO 2009/126278 | * | 10/2009 | ............. B01J 23/85 |
| WO | 20107591 A2 | | 1/2010 | |
| WO | 2013009820 A1 | | 1/2013 | |

OTHER PUBLICATIONS

U.S. Office Action dated Sep. 14, 2021 pertaining to U.S. Appl. No. 14/366,611, filed Jun. 18, 2014, 12 pages.
Werther, J. and Reppenhagen, J., Handbook of Fluidization and Fluid-Particle System, 2003, pp. 1-6, Yang W. (Ed.), Marcel Dekker, New York.
Weeks and Dumbill, Oil and Gas Journal, 1990, pp. 38-45.
International Search Report and Written Opinion for PCT/US2013/024831, dated Jun. 26, 2013, pp. 1-9.
International Preliminary Report on Patentability for PCT/US2013/024831, dated Aug. 26, 2014, pp. 1-6.
Non-Final Office Action dated Sep. 14, 2022, pertaining to U.S. Appl. No. 17/671,779, 21 pgs.

\* cited by examiner

*Primary Examiner* — Patricia L. Hailey
(74) *Attorney, Agent, or Firm* — Dinsmore & Shohl LLP

(57) ABSTRACT

A process for dehydrogenating alkane or alkylaromatic compounds comprising contacting the given compound and a dehydrogenation catalyst in a fluidized bed. The dehydrogenation catalyst is prepared from an at least partially deactivated platinum/gallium catalyst on an alumina-based support that is reconstituted by impregnating it with a platinum salt solution, then calcining it at a temperature from 400° C. to 1000° C., under conditions such that it has a platinum content ranging from 1 to 500 ppm, based on weight of catalyst; a gallium content ranging from 0.2 to 2.0 wt %; and a platinum to gallium ratio ranging from 1:20,000 to 1:4. It also has a Pt retention that is equal to or greater than that of a fresh catalyst being used in a same or similar catalytic process.

16 Claims, No Drawings

RECONSTITUTED DEHYDROGENATION CATALYST SHOWING SLOWED ACTIVITY LOSS WHEN COMPARED WITH FRESH CATALYST

CROSS-REFERENCE TO RELATED APPLICATIONS

This application is a Divisional Application of National Stage Entry application Ser. No. 14/366,611 filed Jun. 18, 2014, which claims priority of International Patent Application PCT/US2013/24831, filed Feb. 6, 2013, which claims priority to U.S. Provisional Application Ser. No. 61/600,764 filed Feb. 20, 2012, the entire disclosures of which are hereby incorporated by reference.

BACKGROUND

Field of the Invention

This invention relates to reconstitution of a deactivated dehydrogenation catalyst, especially a dehydrogenation catalyst comprising a Group 10 transition metal such as platinum (Pt).

Background of the Art

Researchers have long sought methods for reactivating metal-containing catalysts, particularly those including metals that are relatively expensive. For example, U.S. Pat. No. 4,422,954 (Van Peppen) discloses a method for restoring the metal content of a supported noble metal (e.g., palladium (Pd), silver (Ag), platinum (Pt), iridium (Ir), rhodium (Rh), ruthenium (Ru), or osmium (Os)) hydrogenation catalyst. Catalyst supports include alumina ($Al_2O_3$) and silica ($SiO_2$). The method comprises adding an appropriate amount of a noble metal salt (e.g., palladium phenate) of a weak acid to a fluid feed (e.g., phenol) passing across the catalyst. The noble metal salt of a weak acid is reduced to the noble metal under hydrogenation conditions, which include a temperature such as 160 degrees Celsius (° C.), whereas a noble metal salt of a strong acid resists reduction to the noble metal.

U.S. Pat. No. 4,147,660 (Yamauchi, et al.) teaches a method for reactivating a supported platinum group metal (e.g., Pd, Pd or Ru) catalyst by treating the catalyst with at least one agent selected from an inorganic alkaline substance and a reducing substance in an aqueous medium. The inorganic alkaline substance contains at least one alkali metal or alkaline earth metal. The reducing substance is a water-soluble or water-dispersible material such as hydrazine, calcium tartrate or glucose.

U.S. Pat. No. 4,409,122 (Kleuskens, et al.) discloses a process for reactivating spent tellurium-containing oxidic catalysts by mixing a solid particulate tellurium compound such as tellurium oxide with spent catalyst to raise the tellurium content thereof to a value between 90% and 500% of the original catalyst tellurium content. Catalyst reactivation can include calcining a mixture of solid particulate tellurium compound and spent catalyst.

U.S. Pat. No. 3,259,588 (Harvey, et al.) relates in part to reactivation of hydrogenation catalysts that comprise a Group VI or Group VIII metal other than a noble metal on a high surface area support. Reactivation includes impregnation of spent catalysts with a metal salt solution and thereafter thermoactivating (calcining) the impregnated, spent catalyst.

U.S. Pat. No. 2,862,890 (Daugherty, Jr.) teaches reactivation of reforming catalysts such as those containing a small amount of Pt on a metal oxide carrier. Reactivation involves resurfacing deactivated catalyst with an amount of Pt that is relatively small compared to virgin catalyst. Reactivation comprises treating deactivated catalyst with a Pt-containing solution and then calcining the treated catalyst. The amount of Pt-containing solution (e.g., chloroplatinic acid) should be such as to provide 0.01 percent to 0.1 percent by weight (wt %) additional Pt based on final catalyst composition, but less than one half the amount of Pt that was on the deactivated catalyst.

Thus, it is known that dehydrogenation catalysts containing or based on Group 10 elements (as designated according to the current 1 through 18 group numbering scheme of the Periodic Table of the Elements promulgated by the International Union of Pure and Applied Chemistry (IUPAC)) undergo deactivation during use. However, frequent replacement with fresh catalyst is expensive and undesirable. There is, therefore, a continuing need in the art to provide additional methods to enable reuse of these expensive catalysts.

SUMMARY OF THE INVENTION

In one aspect, the present invention provides a process for dehydrogenating alkane or alkylaromatic compounds comprising contacting, in a fluidized bed, an alkane compound or an alkylaromatic compound and a reconstituted dehydrogenation catalyst, such reconstituted dehydrogenation catalyst having been prepared by (a) obtaining a dehydrogenation catalyst comprising platinum and gallium on an alumina-based support, the dehydrogenation catalyst having been previously fresh but having become at least partially deactivated; (b) impregnating the at least partially deactivated dehydrogenation catalyst with a platinum salt solution to form an impregnated dehydrogenation catalyst; and (c) calcining the impregnated dehydrogenation catalyst at a temperature ranging from 400° C. to 1000° C.; (b) and (c) being carried out under conditions suitable to form a reconstituted dehydrogenation catalyst having (i) a platinum content ranging from 1 part per million (ppm), based on weight of catalyst, to 500 ppm, based on weight of catalyst; (ii) a gallium content ranging from 0.2 wt % to 2.0 wt %; and (iii) a ratio of platinum to gallium ranging from 1:20,000 to 1:4; wherein the reconstituted dehydrogenation catalyst further exhibits a platinum retention greater than or equal to the platinum retention of a fresh dehydrogenation catalyst when each is used in the same or another, otherwise identical dehydrogenation process.

In another aspect the present invention provides the reconstituted dehydrogenation catalyst described hereinabove and a process to prepare it.

DETAILED DESCRIPTION OF THE EMBODIMENTS

An object of this invention is to prepare a reconstituted Pt—Ga/$Al_2O_3$ catalyst that is less expensive than fresh Pt—Ga/$Al_2O_3$ catalyst, yet sufficiently effective for dehydrogenation, without a need to replace modifier components such as Ga or support materials such as $Al_2O_3$, such that the reconstituted Pt—Ga/$Al_2O_3$ catalyst may be comparable to or even preferred over "fresh," never used Pt—Ga/$Al_2O_3$ catalyst. The inventors hereof have discovered that, when a Pt—Ga catalyst on an alumina-based support, such as $Al_2O_3$ or modified $Al_2O_3$, e.g., silica modified $Al_2O_3$ (see, for example, WO 2005/077867 A, which is incorporated herein by reference in its entirety), is employed for catalytic purposes, particularly in a circulating fluidized bed-based alkane or alkylaromatic dehydrogenation process, the Pt is selectively removed from the catalyst particles, thereby altering the overall catalyst composition and in particular the ratio of platinum to gallium. Based on this understanding, the inventors have developed a catalyst that demonstrates remarkably improved retention of the Pt metal on the catalyst support following the reconstitution process, in comparison with the retention exhibited by an otherwise equivalent "fresh" (neither partially deactivated nor reconstituted, as described further hereinbelow) catalyst, which means that deactivation due to Pt loss is delayed following the catalyst reconstitution described herein, in comparison with the deactivation rate suffered by fresh catalyst. Thus, the invention includes, in various aspects, a catalyst composition, a process for preparing it, and a dehydrogenation process using it.

The method comprises impregnating an "at least partially deactivated" (i.e., "used" or "spent") Pt—Ga/$Al_2O_3$ catalyst. Synonyms used herein for "at least partially deactivated" include common industry terms "used" or "spent," and the phrase is defined herein as referring to a catalyst that has shown a measurable decrease in its activity during use for its catalytic purpose (for example, a dehydrogenation process), i.e., a catalyst that now exhibits a measurably lowered conversion of the material upon which its catalytic activity has previously been directed, such conversion reduction being primarily due to loss of the catalyst's catalytically active component. This impregnation step is carried out by contacting the used catalyst with an amount of platinum, preferably a Pt-containing compound, which is a Pt-containing compound including but not limited to tetraamineplatinum (II) nitrate, platinum (II) nitrate, chloroplatinic acid, platinum (II) acetylacetonate, and combinations thereof. The amount of the post-calcination Pt is desirably from 1 ppm to 500 ppm, based on weight of catalyst, preferably from 40 ppm to 400 ppm, more preferably from 100 ppm to 400 ppm, and most preferably from 150 ppm to 300 ppm; and post-calcination gallium is preferably within a range of from 0.2 wt % to 2.0 wt %, and more preferably from about 0.8 wt % to 2.0 wt %. This means that the post-calcination ratio of platinum to gallium desirably ranges from 1:20,000 to 1:4, preferably from 1:500 to 1:5, more preferably from 1:200 to 1:20, and most preferably from 3:400 to 3:80. For purposes herein, the content of Ga, expressed as the weight percent content of Ga in the used catalyst, may be assumed to be approximately equal to the starting content of the "fresh" catalyst, as very little, if any, Ga is lost during catalyst use. In fact, it was discovered in conjunction with the present invention that the Pt is preferentially removed during catalyst use, possibly due to volatility of $PtO_2$, migration of metal to the surface of the support in combination with mechanical removal of platinum-containing particles, or some other unknown mechanism(s). In general it is effective to select a target post-calcination Pt weight content that ranges from 60% to 150%, desirably from 60% to 120%, of the Pt content of fresh Pt—Ga/$Al_2O_3$ catalyst. Impregnation may be carried out by any method known to those skilled in the art, including but not limited to the incipient wetness method, slurry impregnation, chemical vapor deposition, a combination thereof, or the like.

Following the impregnation, the impregnated catalyst may optionally be allowed to age, i.e., to remain quiescent, for a time. This time may range from 1 hour (h) to 24 h. In certain particular embodiments, the time may range from 4 h to 16 h.

Once the catalyst has been impregnated and, if desired, aged, it may then be calcined. Those skilled in the art will understand that it is traditional to include a pre-calcination drying step of some type, in order to remove solvent. Removal of the solvent helps to prevent problems that may arise when a solvent-containing catalyst is directly calcined. In practice, the drying and calcinations stages may overlap as to temperature, particularly if temperature is ramped. In general, drying may occur during exposure of the impregnated catalyst to temperatures ranging from room (ambient) temperature to a temperature ranging up to 150° C. During this drying the catalyst is not chemically transformed. Chemical transformation does, however, occur during calcination, resulting in conversion of the Pt salt with which the catalyst is impregnated to platinum oxide (PtO) and/or platinum metal (Pt). The calcination may be carried out at any effective temperature ranging from 400° C. to 1000° C. In particular embodiments the temperature may range from 450° C. to 1000° C., and more preferably from 500° C. to 800° C., and most preferably from 600° C. to 800° C. Calcination is effectively carried out under an atmosphere comprising oxygen, preferably air. Time is preferably from 20 minutes to 720 minutes, more preferably from 40 minutes to 360 minutes. Means conventionally used by or known to those skilled in the art may be selected. It is generally desired that the alumina-based catalyst support be affected or altered as little as possible by the calcination conditions; therefore, use of an alumina-based support, particularly one that is modified with silica and having a surface area of less than 150 meters squared per gram ($m^2$/g), preferably also a Davison Attrition Index below 14, may be, in some embodiments, particularly useful. Those skilled in the art will be aware of the performance of certain alumina phases under a variety of temperature conditions and are referred to U.S. Pat. No. 7,235,706 as a general reference.

The foregoing inventive reconstitution process may be repeated until yield accomplished using the catalyst is reduced to a level that is unsatisfactory or undesirable, or until catalyst attrition results in particles ("fines") that are sufficiently small (e.g., less than 20 micrometers (μm)) that they are simply lost in the dehydrogenation process, e.g., they are effectively entrained in the gas used in the fluidized bed and are not effectively recoverable. Absent an effective means of recovering such particles it has heretofore been conventional and unavoidable to, at that point, replace the catalyst with fresh catalyst.

The reconstituted catalyst of the invention may be particularly useful to facilitate a circulating fluidized bed dehydrogenation of alkanes, alkylaromatics, or combinations thereof. The circulating fluidized bed (CFB) dehydrogenation process for this application uses, in preferred but non-limiting embodiments, a system which comprises mainly a dehydrogenation reactor and a regenerator, both fluid bed based. In this process, one or more hydrocarbons selected from the group consisting of paraffinic hydrocarbons and alkylaromatic hydrocarbons contact the inventive dehydrogenation catalyst at reaction temperature and in concurrent flow through a dehydrogenation reactor. The temperature in the dehydrogenation reactor is typically from 500° C. to 800° C., and the pressure in the dehydrogenation reactor is frequently from 5 to 50 pounds per square inch absolute (psia) (about 34.5 kilopascals (kPa) to about 345 kPa). Catalyst residence time in the dehydrogenation reactor may typically vary from 0.5 seconds (sec) to 240 sec. The catalyst/gas products are separated by high efficiency cyclones. After the separation, the catalyst is stripped with an inert gas before being sent to a regenerator. In the regenerator vessel, coke on the catalyst is removed by combustion in an oxygen-containing environment (usually air), and catalyst is heated by additional fuel to the target temperature. Catalyst circulates back to the reactor, carrying the necessary heat for the dehydrogenation reaction. For additional generalized information on catalytic dehydrogenations carried out in circulating fluidized beds, those skilled in the art are referred to, for example, US Patent Publication 2005/0177016 A1; International Patent Publication WO 2005/077867 (corresponding to US Patent Publication 2008/0194891 A1); and International Patent Publication WO 20107591 A1.

Use of the reconstituted catalyst of the invention offers renewed or regenerated activity where the catalyst is exhibiting reduced activity due to use, particularly where it has been used in a dehydrogenation such as is described hereinabove, such that yield (activity) has been measurably reduced. In the case of a propane dehydrogenation, for example, the used or spent ("at least partially deactivated") catalyst may be reconstituted according to the invention and cycled back into the system, where it may exhibit a propane dehydrogenation activity that is at least 2% absolute propane conversion greater than that of the at least partially deactivated catalyst under otherwise identical dehydrogenation conditions. In another embodiment the propane dehydrogenation activity exhibited by the reconstituted catalyst may be greater by an amount equal to or more than 5% on the same basis. This may reasonably be construed as implying that, in certain embodiments, the inventive catalyst may then or thereafter be exhibiting a loss in activity that is relatively delayed when compared to the loss in activity exhibited by fresh catalyst under otherwise identical dehydrogenation conditions.

The foregoing process may be, and preferably is, practiced without use of precursor steps that remove extraneous materials, such as impurities picked up from the reactor metal or refractory or the feed stream, deposited on catalyst surfaces. These precursor steps include washing a catalyst that has extraneous materials deposited thereon with an organic solvent, an acid or a base to remove the extraneous materials. Eliminating such precursor steps concurrently eliminates their cost and contributes to economic desirability of the foregoing method.

EXAMPLES

Example 1 (Ex 1)

In an oven operating at a set point temperature of 350° C., pre-dry an 15.8 g aliquot of used (i.e., "at least partially deactivated") catalyst containing 92 ppm Pt, 0.25 wt % potassium and 1.6 wt % Ga oxide on an alumina/silica support (1.5 wt % silica, based upon combined weight of alumina and silica) (SIRALOX™ 1.5/70, commercially available from Sasol) for 2 h. Remove the aliquot from the oven and allow it to cool to ambient temperature (nominally 25° C.). Into a 50 milliliter (mL) beaker equipped with a magnetic stirbar, charge 0.020 g tetraammine Pt (II) nitrate and 20 g deionized (DI) water. Stir contents of the 50 mL beaker until the Pt nitrate dissolves to form a visually uniform solution. After the aliquot of used catalyst is cooled to ambient temperature, transfer it into a 50 mL glass beaker. Add, with stirring, 3.5 g of the Pt solution to the pre-dried used catalyst in small aliquots, less than 1 mL each, to effect dispersion of the metal nitrate into and onto the pre-dried material. Discontinue stirring and place the uncovered 50 mL beaker containing the wetted catalyst in a fume hood overnight at ambient temperature.

Remove the beaker from the fume hood, and dry its contents at 120° C. for 4 h before calcining the contents under air for 4 h at 750° C. The calcined material has been reconstituted with 200 additional parts Pt per million parts material (ppm, based on total catalyst). This is a calculated value that may be confirmed analytically by X-ray fluorescence (XRF) or elemental analysis using inductively coupled plasma mass spectrometry (ICP-MS).

Evaluate performance of the catalyst using a plug flow reactor modified to test catalysts under short contact time between reactant and catalysts by exposing 0.5 g of the catalyst, mixed with 1 g of silicon carbide (SiC) as a diluent, to a feedstream that comprises 90 mole percent (mol %) propane and 10 mol % nitrogen, each mol % being based upon combined moles of propane and nitrogen and flows at a flow rate of 10 reciprocal hours ($hr^{-1}$), a reaction pressure of one atmosphere (atm) (101.3 kilopascals (KPa)), and a reaction temperature of 600° C. Regenerate the catalyst by exposing it to a temperature of 700° C. with an air flow of 150 standard cubic centimeters per minute for a period of 900 sec.

Employ gas chromatography to analyze for effluent composition. Conduct sampling after 20 sec of catalyst time on stream. The compounds analyzed include methane, ethane, ethylene, propane, propylene, $C_4$ compounds (butane and butenes), $C_5$ compounds, $C_6$ compounds, $N_2$ internal standard, CO and $CO_2$.

Calculate alkane conversion and dehydrogenation selectivity to corresponding alkenes (e.g., ethane to ethylene, propane to propylene, or butane to butylene) as follows:

Alkane conversion=Total moles of alkane equivalents in product per min/(Moles of alkane in effluent per min+ Total moles of alkene equivalents in product per min)

Selectivity for Alkene=Moles alkane equivalents in alkene per min/Total moles alkane equivalents in products per min Also determine Pt retention using a Davison 1-inch Jet Cup Attrition Test Unit. For further discussion of the Jet Cup Attrition Test method, which is applied widely in the fluid catalytic cracking (FCC) industry, see, e.g., Werther, J. and Reppenhagen, J., *Handbook of Fluidization and Fluid-Particle System*, Yang W. (Ed.), Marcel Dekker, New York, 2003; and S. A. Weeks and P. Dumbill, *Oil Gas J.* 88 (1990), pp. 38-45. Prior to the determination, calcine the catalyst at 500° C. for 2 h. 6 g of catalyst ("Starting Material") is then loaded to a jet cup and attached to the unit. The catalyst is subjected to a $N_2$ stream which has been tangentially injected into the jet cup with a linear velocity of 580 feet per second (ft/sec) and temperature of 30° C. Moisture is added to the system to keep the relative humidity at 60%. The solid particles are accelerated by the gas and moved around inside the wall of the cup. The fines in the catalyst and the fines generated are carried away and collected in a thimble. The catalyst is under $N_2$ jet treatment for 1 hr. At the end of the test, the catalyst remaining in the jet cup ("Cup Materials") is collected. Pt retention is determined by the Pt concentration on catalyst before and after the Jet Cup Attrition Test. The collected cup materials are sent for Pt analysis by X-Ray fluorescence (XRF) or ICP-MS along with the fresh catalyst. The Pt retention reported in Table 1 is calculated as the ratio of Pt concentration in Cup Materials to Pt concentration of the starting materials. Record results in Table 1. The Jet Cup Attrition Test as used to determine Pt retention is designed to achieve accelerated Pt loss via severe laboratory experimental conditions, for generation of a ranking according to relative Pt retention.

Example 2 (Ex 2)

Replicate Example 1, but change the amount of Pt solution added to the pre-dried material to effect addition of 108 parts Pt per million parts overall catalyst weight. Record results in Table 1.

Comparative Example 1 (CEx 1)

Replicate Example 1, but use a fresh catalyst containing 200 ppm Pt. Record results in Table 1.

Comparative Example 2 (CEx 2)

Replicate Example 1, but with used catalyst that has been regenerated in air, and not reconstituted according to the present invention.

TABLE 1

Propane dehydrogenation performance at 600° C., WHSV* = 10 h$^{-1}$, catalyst time on stream = 20 sec and Pt retention for fresh and reconstituted catalysts.

| Ex/CEx | Catalyst | Propane Conversion (%) | Selectivity to Propylene (%) | Pt Retention (%) |
|---|---|---|---|---|
| CEx 1 | Fresh Catalyst | 41.79 | 99.23 | 46 |
| CEx 2 | Used Catalyst | 36.59 | 99.18 | — |
| Ex 1 | 200 ppm Pt added to the used catalyst | 40.81 | 99.26 | 76 |
| Ex 2 | 108 ppm Pt added to the used catalyst | 39.06 | 99.23 | 70 |

*WHSV = weight hourly space velocity of propane

What is claimed is:

1. A dehydrogenation catalyst composition comprising a reconstituted platinum/gallium catalyst on an alumina-based support,
the reconstituted platinum/gallium catalyst having been prepared by a process comprising
   (a) obtaining a dehydrogenation catalyst comprising platinum and gallium on an alumina-based support, the dehydrogenation catalyst having been previously fresh but having become at least partially deactivated;
   (b) impregnating the at least partially deactivated dehydrogenation catalyst with a solution consisting of platinum salt in water to form an impregnated dehydrogenation catalyst; and
   (c) calcining the impregnated dehydrogenation catalyst at a temperature ranging from 400° C. to 1000° C.;
   (b) and (c) being carried out under conditions suitable to form a reconstituted dehydrogenation catalyst having (i) a platinum content ranging from 1 part per million, based on weight of catalyst, to 500 parts per million, based on weight of catalyst; (ii) a gallium content ranging from 0.2 wt % to 2.0 wt %; and (iii) a ratio of platinum to gallium ranging from 1:20,000 to 1:4;
   wherein the reconstituted dehydrogenation catalyst further exhibits a platinum retention greater than or equal to the platinum retention of a fresh dehydrogenation catalyst when each is used in the same or another, otherwise identical dehydrogenation process.

2. A process to prepare a catalyst comprising:
   (a) obtaining a dehydrogenation catalyst comprising platinum and gallium on an alumina-based support, the dehydrogenation catalyst having been previously fresh but having become at least partially deactivated by the selective removal of platinum from the dehydrogenation catalyst, wherein the gallium content of the at least partially deactivated dehydrogenation catalyst is approximately equal to the gallium content of the previously fresh dehydrogenation catalyst;
   (b) impregnating the at least partially deactivated dehydrogenation catalyst with a solution consisting of a platinum salt in water to form an impregnated dehydrogenation catalyst; and
   (c) calcining the impregnated dehydrogenation catalyst at a temperature ranging from 400° C. to 1000° C.;
   (b) and (c) being carried out under conditions suitable to form a reconstituted dehydrogenation catalyst having (i) a platinum content ranging from 1 part per million, based on weight of catalyst, to 500 parts per million, based on weight of catalyst; (ii) a gallium content ranging from 0.2 wt % to 2.0 wt %; and (iii) a ratio of platinum to gallium ranging from 1:20,000 to 1:4;
   wherein the reconstituted dehydrogenation catalyst further exhibits a platinum retention greater than or equal to the platinum retention of a fresh dehydrogenation catalyst when each is used in the same or another, otherwise identical dehydrogenation process.

3. The process of claim 2, further comprising a step, between (b) and (c), of drying the impregnated dehydrogenation catalyst at a temperature ranging from 50° C. to 150° C.

4. The process of claim 2, wherein the platinum content of the reconstituted dehydrogenation catalyst ranges from 40 parts per million, based on weight of catalyst, to 400 parts per million, based on weight of catalyst, and the ratio of platinum to gallium content ranges from 1:500 to 1:5.

5. The process of claim 2, wherein the platinum content of the reconstituted dehydrogenation catalyst ranges from 150 parts per million, based on weight of catalyst, to 300 parts per million, based on weight of catalyst, and the ratio of platinum to gallium content ranges from 3:400 to 3:80.

6. The process of claim 2, wherein the alumina-based support has a Davison Attrition index of less than 14.

7. The process of claim 2, wherein the alumina-based support is modified with silica.

8. The process of claim 2, wherein the gallium content ranges from 0.8 wt % to 2.0 wt %.

9. The process of claim 2, wherein the calcining comprises calcining the impregnated dehydrogenation catalyst at a temperature ranging from 600° C. to 800° C.

10. The process of claim 9, wherein the calcining is carried out for a time of from 20 to 720 minutes.

11. The process of claim 9, wherein the calcining is carried out for a time of from 40 to 360 minutes.

12. The process of claim 2, wherein the platinum salt is selected from the group consisting of tetraamine platinum (II) nitrate, platinum (II) nitrate, platinum (II) acetylacetonate, and combinations thereof.

13. The process of claim 2, wherein the process excludes precursor steps that remove extraneous materials deposited on surfaces of the at least partially deactivated dehydrogenation catalyst.

14. The process of claim 2, wherein the calcination is carried out under an atmosphere comprising oxygen.

15. The process of claim 14, wherein the calcination is carried out in air.

16. The process of claim 2, wherein the at least partially deactivated dehydrogenation catalyst has a ratio of platinum to gallium that is less than a ratio of platinum to gallium of the previously fresh dehydrogenation catalyst.

\* \* \* \* \*